United States Patent [19]

Welebir

[11] 4,423,236

[45] Dec. 27, 1983

[54] 5,6,-0-ISOALKYLIDENE ASCORBIC ACID DERIVATIVES

[75] Inventor: Andrew J. Welebir, Falls Church, Va.

[73] Assignee: National Foundation for Cancer Research, Inc., Bethesda, Md.

[21] Appl. No.: 314,423

[22] Filed: Oct. 23, 1981

Related U.S. Application Data

[63] Continuation-in-part of Ser. No. 177,940, Aug. 14, 1980, abandoned.

[51] Int. Cl.³ .................. C07D 407/00; C07D 307/62
[52] U.S. Cl. .................................... 549/320; 549/315; 549/317; 549/318; 549/321; 424/280
[58] Field of Search ............... 549/315, 313, 320–321, 549/318, 317

[56] References Cited

U.S. PATENT DOCUMENTS

| | | | |
|---|---|---|---|
| 2,539,483 | 1/1951 | Rushin | 548/344 |
| 3,965,199 | 6/1976 | Amann et al. | 549/300 |
| 3,968,233 | 7/1976 | Garzia | 549/321 |
| 4,111,958 | 9/1978 | Crawford | 549/306 |
| 4,146,651 | 3/1979 | Bharucha et al. | 549/315 |
| 4,302,395 | 11/1981 | Brois et al. | 549/321 |
| 4,350,637 | 9/1982 | Martel et al. | 549/321 |

FOREIGN PATENT DOCUMENTS

| | | | |
|---|---|---|---|
| 1365959 | 6/1964 | France | 549/313 |
| 1026403 | 4/1966 | United Kingdom | 549/313 |

OTHER PUBLICATIONS

Johnston et al., Journ. Med. Chem., Jul. 1971, pp. 600–614.

*Primary Examiner*—Ethel G. Love
*Attorney, Agent, or Firm*—Fidelman, Wolffe & Waldron

[57] ABSTRACT

Novel condensation products between enediol ketolactones such as 5,6-0-isopropylidene ascorbic acid and 2-chloroethyl isocyanates are shown to have potent antitumor activity probably without the release of alkylating agents in vivo. While the structures of the products are not readily elucidated, activity is found to exceed that of BCNU (bis-(2-chloroethyl)-N-nitrosourea) and parallel that of the toxic and highly effective nitrosourea, MeCCNU (1-(4-trans-methylcyclohexyl)-3-(2-chloroethyl)-3-nitrosourea). Preferred compounds are condensation products of

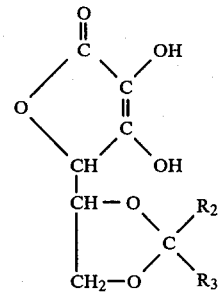

(A)

wherein $R_2$ and $R_3$ are a lower alkyl group containing 1 to 3 carbon atoms or H and

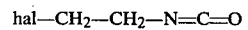

(B)

wherein hal is I, Br or Cl.

5 Claims, No Drawings

5,6,-0-ISOALKYLIDENE ASCORBIC ACID DERIVATIVES

RELATED APPLICATIONS

This application is a continuation-in-part of U.S. Ser. No. 177,940 filed Aug. 14, 1980, now abandoned.

DESCRIPTION

1. Technical Field

The present invention relates condensation products between enediol ketolactones and 2-haloethyl isocyanates and pharmaceutically acceptable salts thereof as antitumor agents and possible analgesic agents, and more particularly, to condensation products of 5,6-O-isoalkylidene ascorbic acid derivatives with 2-haloethyl isocyanates and pharmaceutically acceptable salts thereof as novel antitumor agents and possibly analgesic agents. The invention also includes pharmaceutical compositions containing these compounds and methods of using them.

2. Background Art

A number of ascorbic acid derivatives have been cited as having antiscorbutic activity and improved lipid solubility (Warnat, et al., U.S. Pat. No. 2,150,140, Edwin, et al., U.S. Pat. No. 2,454,749, Kobayashi, et al., U.S. Pat. No. 3,318,914, Hoseney, et al., U.S. Pat. No. 4,044,154, Weisblatt, U.S. Pat. No. 2,454,747), however, all appear to involve more or less selective esterification of one or more hydroxyl groups on the molecule. Japanese Pat. No. 4,815,605 to Chitose Seiyaku Co., Ltd. reveals the preparation of certain phoshate salts from isopropylidene ascorbic acid, however, no reference is found as to the biological activity of the salts described therein. Furthermore, no reference can be found to any 5,6-O-isoalkylidene ascorbic acid derivative which shows antitumor or analgesic activity.

The only reference found to antitumor agents derived from ascorbic acid by the present inventor includes condensation products between underivatized ascorbic acid and strongly electrophilic conjugated aldehydes, such as glyoxal, methyl glyoxal, phenyl glyoxal, and a number of olefinic aldehydes, such as acrolein and crotonic, maleic, and fumaric aldehydes (Fodor, et al., U.S. Pat. No. 4,238,500). A number of possible complex structures for the biologically active compound or compounds were originally described in the patent literature, and more specific structures were eventually proposed. Ascorbic acid was originally intended as a carrier for methyl glyoxal, which was subsequently to be released in vivo as the active antitumor agent. Free ascorbic acid has also been proposed as a prophylactic treatment for bladder carcinoma (Schlegel, *Ann. N.Y. Acad. Sci.*, 432 (1975).

Many highly effective antitumor agents presently employed in clinical use consist of either complex natural products, cytotoxic antibiotics, nitrosoureas, and other alkylating or mutagenic agents.

One such compound in clinical use, BCNU (bis-(2 chloroethyl)-N-nitrosourea) has been shown to be metabolized into numerous products in vivo, such as 2-chloroethanol, vinyl chloride, acetaldehyde, and dichloroethane from the nitrosated side of the molecule (T. P. Johnston et al, *J. Med. Chem.*, 18: 634 (1975)). The immediate precursor of these metabolites, viz, the 2-chloroethyl carbonium ion, is a powerful alkylating agent and is known to effectively alkylate DNA within one hour after i.v. administration (O. J. Reed, et al., *Cancer Res.* 35: 568 (1975)). The alkylating agent accounts for the mutagenicity and much of the toxicity associated with the use of BCNU and other nitrosoureas.

The second major product resulting fron the hydrolysis of BCNU in vivo is 2-chloroethyl isocyanate, which may account for the carcinostatic effectiveness of BCNU. The carbamoylated products in vivo resulting from the reaction of 2-chloroethyl isocyanate with a number of enzymes may be the possible mode of action. The study of possible "carriers" of 2-chloroethyl isocyanate may, therefore, result in an antitumor agent of practical utility which would not involve the release of a mutagenic alkylating agent.

DISCLOSURE OF THE INVENTION

In a search for such a "carrier," the present inventor has discovered, surprisingly, that reacting 2-chloroethyl isocyanate with an enediol ketolactone, more particularly, a 5,6-O-isoalkylidene ascorbic acid, produces an addition product or products, not readily identifiable, which possess potent antitumor activity, more so than BCNU, and with less toxicity. The potent antitumor activity, furthermore, is exhibited to a much greater degree than other compounds derived from ascorbic acid in the prior art (Fodor, et al, U.S. Pat. No. 4,238,500), possibly because the mammalian system is accustomed to metabolizing excesses of the released methyl glyoxal produced by the compounds of the prior art. 2-Chloroethyl isocyanate and its derivatives are not readily metabolized.

It has further been found by the instant inventor that adducts found with underivatized ascorbic acid and 2-chloroethyl isocyanates are inactive antitumor agents, thus necessitating blockage of the 5,6-O-positions of the molecule before the addition reaction is allowed to take place. Since this portion of the molecule may not be responsible for the antitumor effect, and since blockage of the 5,6-O-nucleophilic position is essential for synthesis, a variety of enediol ketolactones may be expected to exhibit activity.

According to the requirements of the present invention for a process which affords a product possessing potent antitumor activity, compounds of the following formulae are reacted. The enediol ketolactone A is reacted with the 2-haloisocyanate B to form the product:

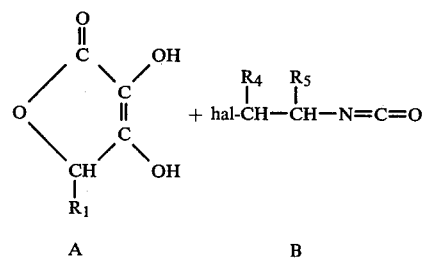

wherein: $R_1$ is an alkyl group containing no nucleophilic substituents, e.g., such as amino, hydroxyl, or sulfhydryl groups but may comprise lower alkyl ethers, lower alkyl esters, or carbonate esters or carboxylic acids or amides, preferably ketals or acetals of the formula:

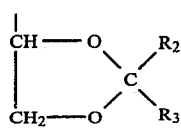

wherein: $R_2$ and $R_3$ are lower alkyl groups containing 1 to 3 carbons or H, preferably a protected ascorbic acid derivative which may be a 5,6-O-isoalkylidene ascorbic acid derivative, and more preferably the 5,6-O-isopropylidene derivative of ascorbic acid:

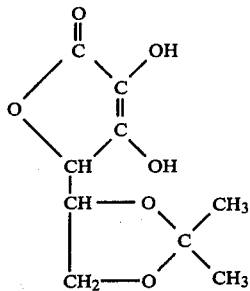

B is preferably 2-chloroethyl isocyanate ($R_4=R_5=H$), however, 2-chloroethyl isocyanates containing alkyl substituents are useful. Hal. is an electron-withdrawing group, such as a halogen, preferably Cl, Br, or I, and more preferably Cl. The inclusion of other substituents which are known in the art to enhance water or lipid solubility, or pharmaceutically acceptable salts, are not beyond the scope of the present invention.

The preferred solvents for the reaction are any solvent in which the final products show solubility with dipolar, aprotic solvents being preferred, such as lower aliphatic ketones, e.g., acetone, DMSO (dimethyl sulfoxide), DMF (dimethyl formamide), and HMPA (hexamethyl phosphoramide), along with other similar solvents, acetone being most preferred.

Reactants (1 part 5,6-O-isoalkylidene ascorbic acid to 2 to 10 parts of isocyanate, preferably 3 to 6 parts isocyanate) are combined in a small amount of solvent (1 part reactants to 1 to 100 parts of solvent) and refluxed under anhydrous conditions, preferably under an inert atmosphere, such as nitrogen or argon. While a large amount of material reacts within a 3 hour period, longer reaction times (up to 72 hours) depending on the solvent, are preferred. Reaction temperatures may range from less than 0° to 150° C., with 30° to 100° C. being preferred.

When the reaction is completed, excess solvent and isocyanate are removed by distillation or evaporation, preferably under vacuum to leave the product as an oily to crystalline solid. This is used directly after combining with an acceptable pharmaceutical carrier in the inhibition of tumor growth in mammalian systems.

While the structure of the compounds of the present invention is not readily elucidated, it is hypothesized that the product does not contain two carbamate linkages, and may, in fact, be a tricyclic compound in the case of the reaction between 5,6-O-isopropylidene ascorbic acid and 2-chloroethyl isocyanate (Scorbethane).

OBJECTS

It is, therefore, an object of the present invention to provide novel compounds having antitumor activity in mammals.

It is another object of the invention to provide condensation products of enediol ketolactones, notable ascorbic acid derivatives with the nucleophilic 5,6-O-positions protected by suitable protecting groups, and 2-haloethyl isocyanates having antitumor activity.

Still another object of the invention is to provide novel effective antitumor agents at low dosages without the in vivo formation of mutagenic alkylating agents.

Yet another object of this invention is to provide novel compounds having analgesic activity.

BEST MODE OF THE INVENTION

Melting points were determined using a Thomas-Hoover capillary melting point apparatus and are uncorrected. Infrared (IR) spectra were obtained using a Perkin Elmer 397 spectrophotometer, and NMR spectra were taken on a Nicolet 200 MHz instrument using $CDCl_3$ as the solvent and TMS as an internal standard.

EXAMPLE 1

Ascorbic acid was converted to the 5,6-O-isopropylidene ascorbic acid derivative employing the method of Solomon(*Experientia* 19: 619 (1963)). A 10 g quantity of L-ascorbic acid (0.054 mol) was added to 100 ml of anhydrous acetone and cooled on an ice bath. Anhydrous HCl was passed through the suspension with vigorous stirring for 0.5 hr. Hexane (80 ml) was added and the mixture was stirred and allowed to settle. The liquid was decanted, and the solid was washed repeatedly with 100 ml volumes of acetone:hexane, 4:7, until all the HCl was removed. The remaining solid (11.3 g, 91%) had a MP of 220° (lit. 222°) and its presence was confirmed by IR and NMR. Other 5,6-O-isoalkylidene ascorbic acids may be synthesized using this procedure.

SCORBETHANE

Condensation products of:

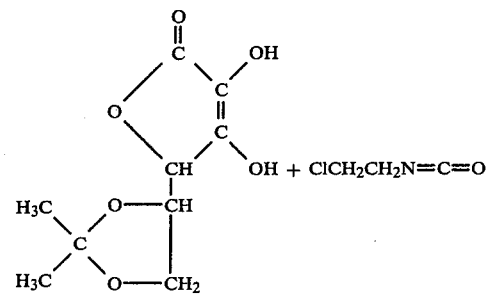

EXAMPLE 2

Scorbethane, the 2-chloroethyl isocyanate adduct of isopropylidene ascorbic acid, was prepared by suspending 2.16 g (0.01 mol) of the isopropylidene derivative in 10 ml of anhydrous acetone, and the reaction vessel was flooded with nitrogen. 2-chloroethyl isocyanate (4.4 g, 0.04 mol) was added and the mixture was refluxed for 65 hours. The solvent was removed in vacuo and the compound was dried in vacuo for 48 hours over KOH. NMR analysis showed a singlet (6H) at 1.3 ppm, a multiplet (9H) at 3.7 ppm, and a multiplet (4H) at 4.1 ppm.

IR showed peaks at 3250 cm$^{-1}$ (N—H), 1790 cm$^{-1}$ (C=O), (1680 cm$^{-1}$ (amide II band), and 1540 cm$^{-1}$ (N—C=O), apparently residual or partially released isocyanate. Other enediol ketolactones undergo an identical reaction.

ANTITUMOR SCREENING

Antitumor screening data were obtained through the National Cancer Institute, Drug Evaluation Branch, National Institutes of Health, Bethesda, Md.

L-1210 lymphoid leukemia tumors, (10$^5$ cells) were implanted in CDF$_1$ mice in accordance with NIH Protocols. The results reported in Tables 1 and 2 are single dose responses with survival being evaluated five days after i.p. injection of Scorbethane (six days after implantation). The compound was injected as a suspension in 10% EtOH, 10% emulphor, and 80% saline. Log kill data indicates the number of tumor cells killed, and 30-day survivors are termed "cured." The degree of antitumor activity is expressed as a ratio of treated animals over control animals using NCI test evaluation numbers, as specified in individual protocols.

Table I shows the remarkable effectiveness of Scorbethane, the adduct found from the reaction of 5,6-O-isopropylidine ascorbic acid and 2-chloroethyl isopropylidene ascorbic acid and 2-chloroethyl isocyanate, against L-1210 lymphocytic leukemia, with results comparable to those observed from MeCCNU. MeCCNU (1-cyclohexyl-3-(2-chloroethyl)-3-nitrosourea) is currently the most effective against L-1210 leukemia and many solid tumor systems. Furthermore, the data show significant superiority over the results observed using BCNU (T/C=184% at 47 mg/kg for L-1210), which has been widely studied in these tumor systems in the art.

TABLE 1

| | | Scorbethane (NSC 325625) v. L-1210 Leukemia | | | | | | | | | | | |
|---|---|---|---|---|---|---|---|---|---|---|---|---|---|
| Dose | Sex | Dose per Injection (mg/kg) | Survival | Log Kills | Cures | No-Takes | Tumored Survivors | Weight Diff. (T/C) | % T/C | Test Eval. | | DAY/DEATHS | |
| 1 | F | 100.00 | 2/6 | Toxic | 0 | 0 | 0 | −5.5 | — | — | 5/3 | 6/1 | 7/1 |
| 2 | F | 50.00 | 5/6 | 5.94 | 3 | 0 | 0 | −6.1 | 235* | 21.2 | 6/1 | 7/1 | |
| 3 | F | 25.00 | 6/6 | 5.94 | 5 | 0 | 0 | −3.5 | 322* | 29.0 | 19/1 | | |
| 4 | F | 12.50 | 6/6 | 5.94 | 2 | 0 | 0 | −1.9 | 252* | 22.7 | 15/2 | 17/1 | 27/1 |
| 5 | F | 6.25 | 6/6 | 4.05 | 0 | 0 | 0 | 0.0 | 147* | 13.3 | 12/2 | 13/1 14/2 | 15/1 |
| 6 | M | 100.00 | 0/6 | Toxic | 0 | 0 | 0 | — | — | — | 4/3 | 5/3 | |
| 7 | M | 50.00 | 5/6 | 5.94 | 0 | 0 | 0 | −5.1 | 100 | 8.0 | 5/1 | 6/3 11/2 | |
| 8 | M | 25.00 | 6/6 | 5.94 | 5 | 0 | 0 | −3.7 | 371* | 29/7 | 23/1 | | |
| 9 | M | 12.50 | 6/6 | 5.94 | 1 | 0 | 0 | −2.0 | 202* | 16.2 | 11/1 | 12/1 14/2 | 15/1 |
| 10 | M | 6.25 | 6/6 | 4.89 | 0 | 0 | 0 | −0.5 | 165* | 13.2 | 12/2 | 13/2 14/1 | 15/1 |
| | | | | | | | | | | Control (Female) | | | |
| | | | | | | | | | | | 7/2 | 8/7 9/12 10/6 | 11/3 |
| | | | | | | | | | | Control (Male) | | | |
| | | | | | | | | | | | 7/1 | 8/21 9/2 | |

*Exceeds the minimum T/C of 125% required to indicate a potential carcinostatic agent Table II shows the effectiveness of Scorbethane vs. the P-1534 leukemia model. This model shows a higher degree of resistance to nitrosoureas than many other leukemia models. Again, activity approximates the activity of MeCCNU, exceeding that of BNCU, without in vivo production of an alkylating species.

TABLE II

| Scorbethane (NSC 325625) v. P-1534 Leukemia | | | | | |
|---|---|---|---|---|---|
| Dose | Sex | Dose per Injection (mg/kg) | Weight Diff. | % T/C | Test Eval. |
| 1 | F | 16.00 | −3.9 | 113 | 11.1 |
| 2 | F | 8.00 | −3.2 | 193* | 19.0 |
| 3 | F | 4.00 | −3.1 | 202* | 19.8 |
| 4 | F | 2.00 | −2.3 | 153* | 15.0 |
| 5 | F | 1.00 | −1.5 | 121 | 11.9 |
| Dose # | | | DAY/DEATHS | | |
| 1 | 10/1 | 11/4 | 13/1 | | |
| 2 | 10/1 | 11/2 | 19/1 | 20/1 | 22/1 |
| 3 | 9/1 | 15/1 | 19/1 | 20/2 | 22/1 |
| 4 | 6/1 | 12/1 | 14/1 | 15/1 | 16/2 |
| 5 | 11/2 | 12/4 | | | |
| | | Controls | | | |
| | 8/1 | 9/13 | 10/16 | 11/6 | |

*Exceeds the minimum 125% required to indicate a potential carcinostatic agent

Similar clinical results can be obtained with the use of the other compounds of the invention.

The nitrosoureas of the invention can be formulated into a form suitable for administration by methods well known in the art. For example, they can be admixed with pharmaceutically acceptable carriers or diluents such as ethanol, lactose, starch, magnesium stearate, tragacanth, gelatin and sodium carboxymethylcellulose, and the resulting mixture or solution may be processed by conventional procedures to pharmaceutical dosage unit forms such as capsules, tablets, powders, pills, ampoules, suppositories and the like.

The compounds of the invention, such as Scorbethane, may be administered orally or parenterally. For example, the drug may be given intravenously by first dissolving the compound to be administered in 0.5–10 ml of ethanol and adding 50–90% water thereto. Further dilution may be made with physiological saline solution or 5% dextrose (USP) with or without the inclusion of an emulsifying agent. Intravenous administration may be continued for a period of up to several hours.

5,6-O-substituted ascorbic acid derivatives and similar compounds can be injected intravenously at dosages of about 0.1–10 mg/kg.

Other parenteral routes of administration may be accomplished using any formulation known in the art that allows for the emulsification, dissolution or suspension of relatively water-insoluble drugs or other compounds prior to parenteral administration.

When given in unit dosage forms orally, the compounds are active when provided in a gelatin capsule or tablet combined with pharmaceutically acceptable binders, fillers or other additives as known in the art.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A chemical composition comprising the addition products obtained through the reaction of an enediol ketolactone of the formula:

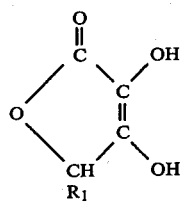

with a 2-haloethyl isocyanate of the formula:

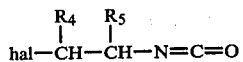

wherein:

hal is selected from the group consisting of I, Br and Cl;

R₁ is selected from the group consisting of hydrogen, alkyl, lower alkyl ether, lower alkyl ester, carbonate ester, carboxylic acid or amide, and a ketal or acetal of the formula:

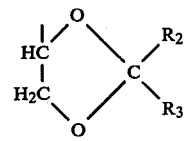

wherein:

R₂, R₃, R₄ and R₅ are selected from the group consisting of lower alkyl containing 1 to 3 carbons and H and may be the same or different.

2. A composition according to claim 1, wherein the enediol ketolactone is a 5,6-O-isoalkylidene ascorbic acid.

3. A composition according to claim 1, wherein the enediol ketolactone is 5,6-O-isiopropylidene ascorbic acid and the isocyanate is 2-chloroethyl isocyanate.

4. A composition according to claim 1, wherein said reaction which forms said addition products is carried out in a dipolar aprotic solvent.

5. A composition according to claim 4, wherein said solvent is a lower aliphatic ketone.

* * * * *